United States Patent [19]
Rainey et al.

[11] Patent Number: 6,111,164
[45] Date of Patent: Aug. 29, 2000

[54] BONE GRAFT INSERT

[75] Inventors: Thomas P. Rainey, Florham; Thomas A. Geary, Oakhurst, both of N.J.

[73] Assignee: Musculoskeletal Transplant Foundation, Holmdel, N.J.

[21] Appl. No.: 08/778,265

[22] Filed: Jan. 2, 1997

Related U.S. Application Data

[60] Provisional application No. 60/020,240, Jun. 21, 1996.

[51] Int. Cl.[7] .................................. A61F 2/28; A61F 2/44
[52] U.S. Cl. .................................. 623/16; 623/17
[58] Field of Search ................... 623/16, 17, 18; 606/60, 61, 72, 74

[56] References Cited

U.S. PATENT DOCUMENTS

| | | | |
|---|---|---|---|
| 4,349,921 | 9/1982 | Kuntz | 623/17 |
| 4,834,757 | 5/1989 | Brantigan | 623/17 |
| 5,015,247 | 5/1991 | Michelson | 606/61 |
| 5,059,193 | 10/1991 | Kuslich | 606/61 |
| 5,062,845 | 11/1991 | Kuslich et al. | 606/80 |
| 5,112,354 | 5/1992 | Sires | 623/16 |
| 5,306,309 | 4/1994 | Wagner et al. | 623/17 |
| 5,320,644 | 6/1994 | Baumgartner | 623/17 |
| 5,423,825 | 6/1995 | Levine | 606/86 |
| 5,439,684 | 8/1995 | Prewett et al. | 623/16 |
| 5,593,409 | 1/1997 | Michelson | 623/17 |
| 5,609,636 | 3/1997 | Kohrs et al. | 623/17 |
| 5,645,598 | 7/1997 | Brosnahan, III | 623/17 |
| 5,683,391 | 11/1997 | Boyd | 623/17 |
| 5,814,084 | 9/1998 | Grivas et al. | 623/16 |
| 5,989,289 | 11/1999 | Coates et al. | 623/17 |

*Primary Examiner*—Mickey Yu
*Assistant Examiner*—Tram A. Nguyen
*Attorney, Agent, or Firm*—Rothwell, Figg, Ernst & Kurz, P.C.

[57] ABSTRACT

A bone graft insert for graft in a patient includes a dowel formed of cortical bone and being substantially free of extraneous cancellous bone material not from the patient. The dowel has a body portion, the body portion having a sidewall portion and a front end with an end face having a surface which is chamfered with respect to the body portion. The body portion has a transverse cavity extending therethrough between opposite sides of the sidewall portion for receiving allograft or the patient's autogenous tissue.

13 Claims, 2 Drawing Sheets

BONE GRAFT INSERT

CROSS-REFERENCE TO RELATED APPLICATION

The present application is a continuation-in-part of U.S. provisional application Ser. No. 60/020,240 filed Jun. 21, 1996.

BACKGROUND OF THE INVENTION

1. Field of the Invention

The present invention relates to the field of bone graft inserts.

2. Description of the Background Art

U.S. Pat. No. 4,950,296 discloses combined cortical and cancellous bone grafting units and methods of making same. The units disclosed therein have an elongated cylindrical cortical body member with flat, planar ends and a cylindrical cavity extending transverse to the axis of the body in which is packed a cancellous bone plug.

There remains a need in the art for improvements in bone graft inserts.

SUMMARY OF THE INVENTION

According to the present invention, a bone graft insert for graft in a patient comprises a dowel formed of cortical bone and being substantially free of extraneous cancellous bone material not from the patient. The dowel has a body portion, the body portion having a sidewall portion, a front end with an end face having a surface which is chamfered with respect to the body portion, and a back end opposite the front end. The back end of the dowel includes a guide pin-receiving opening which extends substantially longitudinally from the back end into the body portion of the dowel. The guide pin-receiving opening is sized and positioned for removably receiving a guide pin for positioning the dowel into a bone opening for grafting. The body portion has a transverse cavity extending therethrough between opposite sides of the sidewall portion for receiving the patient's autogenous tissue.

DETAILED DESCRIPTION OF THE PREFERRED EMBODIMENTS

Figure 1A:
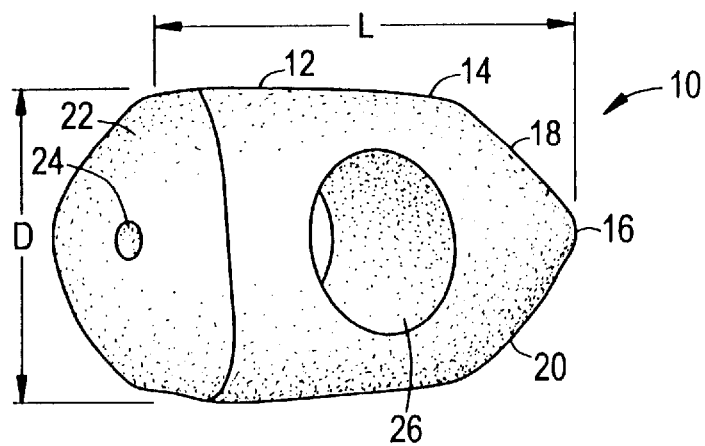
FIG. 1A is a perspective view of a bone graft insert in accordance with the present invention.

A bone graft insert in accordance with the present invention includes a dowel 10 having a body portion 12 with a sidewall portion 14. See FIGS. 1A, 1B and 1C. Dowel 10 is formed of cortical bone and is substantially free of extraneous cancellous bone material such as the cancellous plug insert described in U.S. Pat. No. 4,950,296, incorporated herein by reference.

In accordance with one embodiment, the dowel is formed of a material consisting essentially of cortical bone which is substantially free of extraneous cancellous bone material.

Dowel 10 has a front end 16 with an angled end face 18 having a surface 20 which is chamfered with respect to body portion 12. The sidewall 14 can be substantially cylindrical or have any other suitable shape. Surface 20 can be peripherally or circumferentially chamfered adjacent sidewall 14. Surface 20 can be angled with respect to sidewall 14 at an angle α of less than about 45°, preferably about 5–25°.

Dowel 10 has a back end 22 opposite front end 16. Back end 22 may include a guide pin-receiving opening 24 extending from the back end substantially longitudinally into dowel 10. The guide pin-receiving opening 24 is sized and positioned for removably receiving a guide pin for positioning the dowel into a bone opening, such as a vertebral opening made by a surgeon using an endoscopic instrument. After positioning the dowel, the guide pin can be removed from the dowel with the dowel remaining within the bone opening for grafting.

Body portion 12 of dowel 10 has a transverse cavity 26 (intermedullary canal) extending through body portion 12 between opposite sides of the sidewall portion 14 for receiving allograft (e.g., non-cancellous allograft) or a patient's autogenous tissue, such as the patient's own bone material and blood.

In preferred embodiments, cavity 26 is substantially cylindrical, and has a diameter of about 5–15 mm, more preferably about 7–12 mm.

In preferred embodiments, the guide pin-receiving opening 24 is substantially cylindrical, and extends substantially perpendicular to cavity 26, between back end 22 and cavity 26. Opening 24 can have a diameter of about 0.5–5 mm, and preferably extends parallel with sidewall 14 through body portion 12.

In preferred embodiments, dowel 12 has a length of about 1–5 cm, more preferably, greater than about 1.8 cm and less than about 3 cm.

In further preferred embodiments, dowel 10 has a diameter of about 5–30 mm, more preferably about 10–25 mm, and most preferably about 14–20 mm.

Figure 1B:
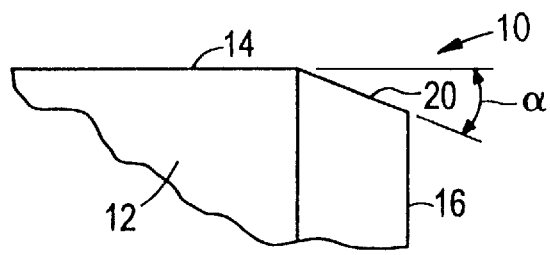
FIG. 1B is a side elevational view, with portions broken away, of a bone graft insert according to the present invention.
Figure 1C:
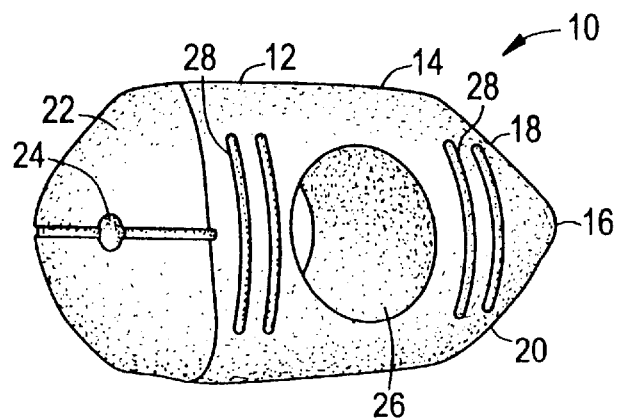
FIG. 1C is a perspective view of a bone graft insert in accordance with another embodiment of the present invention.

In a still further preferred embodiment shown in FIG. 1C, dowel 10 is provided with one or more (preferably a plurality) of circumferentially-located, transverse grooves 28 located on sidewall 14. In the embodiment shown, a pair of grooves 28 is located on fore and aft sides of cavity 26, with a complementary set of grooves located on the side of dowel 10 not shown in FIG. 1C. Each of grooves 28 preferably is about 1 mm wide, but can range in width from about 0.1–2 mm. The depth of each of grooves 28 preferably is about 1 mm, but the depth thereof can be within the range of about 0.1–2 mm. Each of grooves 28 preferably is about 5–10 mm in length. The dowel shown in FIG. 1C has four grooves on the illustrated side and four grooves on the opposite side, for a total of eight grooves. However, any suitable groove arrangement can be utilized. Grooves 28 reduce risk of expulsion (popping out) of the dowel in the posterior direction, and increase the dowel's interbody stability.

Figure 2C:
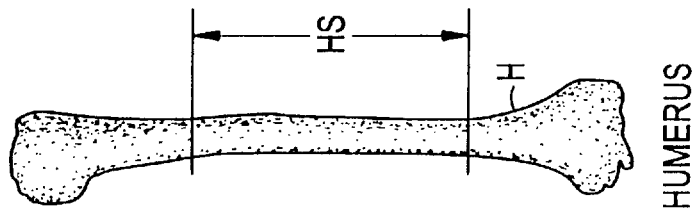
FIGS. 2A, 2B and 2C are respective perspective views of a femur, tibia and humerus, from which bone graft inserts in accordance with the present invention can be formed.
Figure 2B:
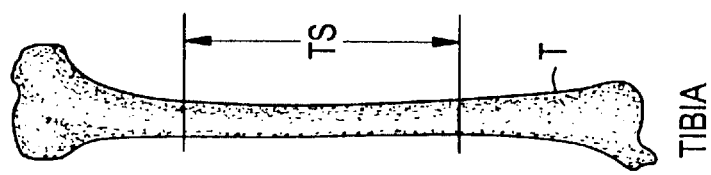
Figure 2A:
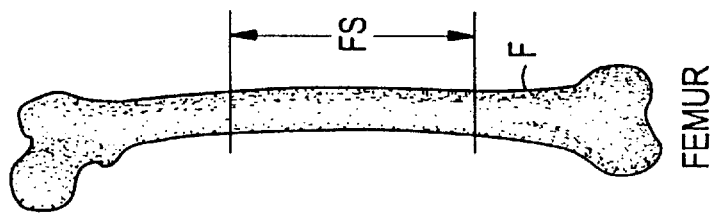

The bone graft insert in accordance with the present invention, as shown in FIGS. 1A, 1B and 1C, can be formed from sections FS, HS or TS respectively from the shaft a femur F, humerus H or tibia T, shown respectively in FIGS. 2A, 2B and 2C, depending on the diameter of the dowel to be formed. Larger diameter dowels are primarily formed from the femur and tibia, while smaller diameter dowels can be formed from the humerus.

A dowel in accordance with the present invention can be cut through the shaft of the selected bone in an anterior direction (through the M-L plane, from posterior to anterior).

The intermedullary canal of the dowel is cleared of all marrow particulate and cancellous bone to form the cavity 26 shown in FIGS. 1A and 1C, which can be filled by the physician with allograft or a patient's autogenous tissue, including blood.

The bone material from which a dowel in accordance with the present invention is formed preferably is aseptic and substantially pure bone mineral, i.e., is substantially protein-free, substantially lipid-free and substantially blood-free. Advantageously, the material from which a dowel in accordance with the present invention is prepared is processed aseptically in a level 10 clean room utilizing a system that includes one or more ultrasonic baths, ethanol treatment, antibiotic soap, and blood/lipid removal steps, all of which are known in the art.

EXAMPLES

Dowels as shown in FIG. 1 were prepared with the following dimensions:

| Diameter | Length |
|---|---|
| 14 mm | >1.8 cm |
| 16 mm | >1.8 cm |
| 18 mm | >1.8 cm |
| 20 mm | >1.8 cm |

The present invention permits the physician to place the patient's autogenous tissue composites against the end plates of vertebral bodies during a vertebral graft, thus facilitating speedier bone graft fusion.

Because many modifications, variations and changes in detail may be made to the desired embodiments, it is intended that all matter in the foregoing description and shown in the accompanying drawings be interpreted as illustrative and not in a limiting sense.

What is claimed is:

1. A bone graft insert for graft in a patient comprising:
   a dowel having a body portion with a length of about 1–5 cm and a diameter of about 5–30 mm, the body portion having a sidewall portion, the dowel being formed of cortical bone and being substantially free of extraneous cancellous bone material not from said patient;
   said dowel having a front end with an end face having a surface which is chamfered with respect to said body portion;
   said body portion having a transverse cavity extending through the body portion between opposite sides of said sidewall portion for receiving a material selected from the group consisting of allograft and autogenous tissue from said patient, wherein said cavity is substantially cylindrical, and has a diameter of about 5–15 mm;
   wherein said dowel has a back end opposite said front end, said back end including a guide pin-receiving opening in said back end, which guide pin-receiving opening extends substantially longitudinally from said back end into the body portion of said dowel, said guide pin-receiving opening being sized and positioned for removably receiving a guide pin for positioning the dowel into a bone opening for grafting.

2. The insert of claim 1, further including at least one substantially transverse groove on said sidewall portion.

3. The insert of claim 2, including a plurality of substantially transverse grooves located substantially circumferentially on said sidewall portion.

4. The insert of claim 3, wherein said grooves are located on opposite sides of said cavity.

5. The insert of claim 4, wherein said grooves are about 1 mm wide, about 1 mm deep, and about 5–10 mm in length.

6. A bone graft insert in a patient comprising:
   a dowel having a body portion with a length of about 1.8–3 cm and a diameter of about 10–25 mm, the body portion having a sidewall portion, the dowel being formed of cortical bone and being substantially free of extraneous cancellous bone material not from said patient;
   said dowel having a front end with an end face having a surface which is chamfered with respect to said body portion;
   said body portion having a transverse cavity extending through the body portion between opposite sides of said sidewall portion for receiving a material selected from the group consisting of allograft and autogenous tissue from said patient;
   wherein said dowel has a back end opposite said front end, said back end including a guide pin-receiving opening in said back end, which guide pin-receiving opening extends substantially longitudinally from said back end into the body portion of said dowel, said guide pin-receiving opening being sized and positioned for removably receiving a guide pin for positioning the dowel into a bone opening for grafting, and
   wherein said cavity is substantially cylindrical, and has a diameter of about 7–12 mm.

7. A bone graft insert for graft in a patient comprising:
   a dowel having a body portion, the body portion having a sidewall portion, the dowel being formed of cortical bone and being substantially free of extraneous cancellous bone material not from said patient;
   said dowel having a front end with an end face having a surface which is chamfered with respect to said body portion;
   said body portion having a transverse cavity extending through the body portion between opposite sides of said sidewall portion for receiving a material selected from the group consisting of allograft and autogenous tissue from said patient;
   wherein said dowel has a back end opposite said front end, said back end including a guide pin-receiving opening in said back end, which guide pin-receiving opening extends substantially longitudinally from said back end into the body portion of said dowel, said guide pin-receiving opening being sized and positioned for removably receiving a guide pin for positioning the dowel into a bone opening for grafting;
   wherein said guide pin-receiving opening is substantially cylindrical in shape, is substantially perpendicular to said transverse cavity, and has a diameter of from about 0.5–5 mm.

8. A bone graft insert for graft in a patient comprising:
   a dowel having a body portion, the body portion having a substantially cylindrical sidewall portion, the dowel being formed of cortical bone and being substantially free of extraneous cancellous bone material not from said patient;
   said dowel having a front end with an end face having a surface which is chamfered with respect to said body portion;
   said body portion having a transverse cavity extending through the body portion between opposite sides of said sidewall portion for receiving a material selected from the group consisting of allograft and autogenous tissue from said patient;

wherein said dowel has a back end opposite said front end, said back end including a guide pin-receiving opening in said back end, which guide pin-receiving opening extends substantially longitudinally from said back end into the body portion of said dowel, said guide pin-receiving opening being sized and positioned for removably receiving a guide pin for positioning the dowel into a bone opening for grafting;

wherein said guide pin-receiving opening extends into said dowel substantially parallel with said sidewall, and is substantially centrally located in said back end.

9. The insert of claim 8, wherein said guide pin-receiving opening extends from said back end to said cavity.

10. A bone graft insert for graft in a patient comprising:
   a dowel having a body portion, the body portion having a sidewall portion, the dowel being formed of cortical bone and being substantially free of extraneous cancellous bone material not from said patient;
   said dowel having a front end with an end face having a surface which is chamfered with respect to said body portion;
   said body portion having a transverse cavity extending through the body portion between opposite sides of said sidewall portion for receiving a material selected from the group consisting of allograft and autogenous tissue from said patient;
   wherein said dowel has a back end opposite said front end, said back end including a guide pin-receiving opening in said back end, which guide pin-receiving opening extends substantially longitudinally from said back end into the body portion of said dowel, said guide pin-receiving opening being sized and positioned for removably receiving a guide pin for positioning the dowel into a bone opening for grafting;
   wherein said dowel is formed from a femur shaft, a humerus shaft or a tibia shaft.

11. A bone graft insert for graft in a patient comprising:
   a dowel having a body portion, the body portion having a sidewall portion, the dowel being formed of cortical bone and being substantially free of extraneous cancellous bone material not from said patient;
   said dowel having a front end with an end face having a surface which is chamfered with respect to said body portion;
   said body portion having a transverse cavity extending through the body portion between opposite sides of said sidewall portion for receiving a material selected from the group consisting of allograft and autogenous tissue from said patient;
   wherein said dowel has a back end opposite said front end, said back end including a guide pin-receiving opening in said back end, which guide pin-receiving opening extends substantially longitudinally from said back end into the body portion of said dowel, said guide pin-receiving opening being sized and positioned for removably receiving a guide pin for positioning the dowel into a bone opening for grafting;
   wherein said dowel is aseptic, substantially pure bone mineral which is substantially free of endogenous protein, blood and lipid.

12. A bone graft insert for graft in a patient comprising:
   a dowel having a body portion, the body portion having a sidewall portion, the dowel being formed of a material consisting essentially of cortical bone and being substantially free of extraneous cancellous bone material not from said patient;
   said dowel having a front end with an end face having a surface which is chamfered with respect to said body portion;
   said dowel having a back end opposite said front end, said back end including a guide pin-receiving opening in said back end, which guide pin-receiving opening extends substantially longitudinally from said back end into the body portion of said dowel, said guide pin-receiving opening being sized and positioned for removably receiving a guide pin for positioning the dowel into a bone opening for grafting;
   said body portion having a single transverse cavity extending through the body portion between opposite sides of said sidewall portion for receiving a material selected from the group consisting of allograft and a patient's autogenous tissue;
   said body portion including a plurality of substantially transverse grooves located on opposite sides of said sidewall portion between said single transverse cavity and said front end; and
   said body portion including another plurality of substantially transverse grooves located on opposite sides of said sidewall portion between said single transverse cavity and said back end.

13. A process for utilizing a bone graft insert, comprising:
providing a bone graft insert, having:
   a dowel having a body portion, the body portion having a sidewall portion, the dowel being formed of cortical bone and being substantially free of extraneous cancellous bone material not from said patient;
   said dowel having a front end with an end face having a surface which is chamfered with respect to said body portion;
   said dowel having a back end opposite said front end, said back end including a guide pin-receiving opening in said back end, which guide pin-receiving opening extends substantially longitudinally from said back end into the body portion of said dowel, said guide pin-receiving opening being sized and positioned for removably receiving a guide pin for positioning the dowel into a bone opening for grafting;
   said body portion having a single transverse cavity extending through the body portion between opposite sides of said sidewall portion for receiving a material selected from the group consisting of allograft and autogenous tissue from said patient;
   said body portion including a plurality of substantially transverse grooves located on opposite sides of said sidewall portion between said single transverse cavity and said front end; and
   said body portion including another plurality of substantially transverse grooves located on opposite sides of said sidewall portion between said single transverse cavity and said back end;

filling said transverse cavity with said material selected from the group consisting of allograft and said patient's autogenous tissue;

inserting said dowel with said material selected from the group consisting of allograft and said patient's autogenous tissue into a bone opening with a guide pin received within said guide pin-receiving opening; and removing said guide pin from said guide pin-receiving opening while leaving said dowel and said material selected from the group consisting of said allograft and said patient's autogenous tissue positioned within said bone opening.

\* \* \* \* \*